United States Patent
Kaneko et al.

(10) Patent No.: US 8,748,409 B2
(45) Date of Patent: *Jun. 10, 2014

(54) POLYSACCHARIDE DERIVATIVE AND HYDROGEL THEREOF

(75) Inventors: Hiroaki Kaneko, Hino (JP); Masaya Ito, Hino (JP)

(73) Assignee: Teijin Limited, Osaka (JP)

( * ) Notice: Subject to any disclaimer, the term of this patent is extended or adjusted under 35 U.S.C. 154(b) by 1 day.

This patent is subject to a terminal disclaimer.

(21) Appl. No.: 13/263,929

(22) PCT Filed: Apr. 19, 2010

(86) PCT No.: PCT/JP2010/057301
§ 371 (c)(1),
(2), (4) Date: Oct. 11, 2011

(87) PCT Pub. No.: WO2010/119994
PCT Pub. Date: Oct. 21, 2010

(65) Prior Publication Data
US 2012/0035128 A1    Feb. 9, 2012

(30) Foreign Application Priority Data

Apr. 17, 2009    (JP) .................. 2009-101081

(51) Int. Cl.
*A61K 31/70*    (2006.01)
*C07H 5/04*    (2006.01)

(52) U.S. Cl.
USPC .............. 514/54; 536/55.1; 536/55.2; 536/56

(58) Field of Classification Search
USPC ......................................... 536/55.1, 55.2, 56
See application file for complete search history.

(56) References Cited

U.S. PATENT DOCUMENTS

| | | |
|---|---|---|
| 6,610,669 B1 | 8/2003 | Calias et al. |
| 2001/0051149 A1 | 12/2001 | Maingault et al. |
| 2010/0008878 A1 | 1/2010 | Hirai et al. |
| 2011/0178184 A1 | 7/2011 | Kaneko et al. |

FOREIGN PATENT DOCUMENTS

| | | |
|---|---|---|
| EP | 1 681 306 A1 | 7/2006 |
| JP | 2000-051343 A | 2/2000 |
| JP | 2002-519481 A | 7/2002 |
| JP | 2003-518167 A | 6/2003 |
| JP | 2006-296916 | 11/2006 |
| WO | 00/01733 A1 | 1/2000 |
| WO | 01/46265 A1 | 6/2001 |
| WO | 2007/015579 A1 | 2/2007 |
| WO | 2009019840 A1 | 2/2009 |
| WO | 2010/016611 A1 | 2/2010 |

OTHER PUBLICATIONS

Extended European Search Report for Application No. 10764571.5 dated Mar. 1, 2013.

*Primary Examiner* — Elli Peselev
(74) *Attorney, Agent, or Firm* — Sughrue Mion, PLLC

(57) ABSTRACT

Disclosed are a polysaccharide derivative obtained by substituting some of the carboxyl groups of a carboxy polysaccharide with —NH—X—CO—Y—Z; and a hydrogel thereof. Here, X is a $C_{1-10}$ hydrocarbon group, Y is a polyalkylene oxide having oxygen atoms at both ends, and Z is a $C_{1-24}$ hydrocarbon group or —CO—$R^2$, with $R^2$ being a $C_{1-23}$ hydrocarbon group. The hydrogel has excellent viscoelasticity and can be injected into a predetermined location with an injection device such as a syringe, and thus can be advantageously used as a medical gel or an adhesion barrier.

11 Claims, No Drawings

POLYSACCHARIDE DERIVATIVE AND HYDROGEL THEREOF

CROSS REFERENCE TO RELATED APPLICATIONS

This application is a National Stage of International Application No. PCT/JP2010/057301 filed Apr. 19, 2010, the contents of which are incorporated herein by reference in their entirety.

TECHNICAL FIELD

The present invention relates to a polysaccharide derivative obtained by substituting a carboxyl group of a carboxy polysaccharide with a specific substituent, and also to a hydrogel thereof. The polysaccharide derivative of the invention forms a hydrogel in water. The hydrogel has excellent viscoelasticity and is capable of forming an amorphous injectable gel that can be injected into a predetermined location with an injection device such as a syringe, and thus can be advantageously used as a medical gel or an adhesion barrier.

BACKGROUND ART

Carboxy polysaccharides, such as hyaluronic acid and alginic acid, have excellent water solubility together with moderate viscosity, adhesiveness, moisture-retaining properties, and biocompatibility, and thus have been widely used as food additives, medical materials, and additives for cosmetics and commodities, particularly as thickening materials.

Of such carboxy polysaccharides, a common, widely used compound is hyaluronic acid. Hyaluronic acid is a water-soluble polymer, and, for its excellent dispersibility and water-retaining properties, has been used in various fields, including food products, cosmetics, drugs, etc. Further, hyaluronic acid has high safety, and thus has been used, in the medical field, as a raw material for joint lubricants, adhesion barriers, etc.

The formation of an insoluble derivative by modifying carboxyl groups of hyaluronic acid has been known. For example, Patent Document 1 describes a water-insoluble derivative of a polyanionic polysaccharide obtained by mixing a polyanionic polysaccharide containing hyaluronic acid, a nucleophilic agent, and an activator in an aqueous mixture, as well as a method for producing the same.

Further, Patent Document 2 describes a hyaluronic acid amide, a derivative thereof, and a method for producing the same. However, the provision of an injectable gel having high viscoelasticity as in the present invention is nowhere mentioned.

Further, Patent Document 3 discloses a natural wound-healing product containing a polysaccharide polymer and one fatty acid chain attached to the polysaccharide polymer, which undergoes a reversible change of state from a gel to a solution.

However, polysaccharides disclosed in these documents have poor viscoelasticity in an aqueous solution, and it is difficult to use them as hydrogels that can be injected into the body through a small tube like an injection needle.

Further, Patent Document 4 states that a product obtained by modifying carboxymethylcellulose side chains with phosphatidylethanolamine can be used as an adhesion barrier agent, and Patent Document 5 states that a product obtained by modifying hyaluronic acid side chains with phosphatidylethanolamine can be used as an adhesion barrier agent.

PRIOR ART DOCUMENTS

Patent Documents

Patent Document 1: WO 01/046265, specification
Patent Document 2: WO 00/01733, specification
Patent Document 3: JP-A-2000-051343
Patent Document 4: WO 07/015579, specification
Patent Document 5: JP-A-2006-296916

SUMMARY OF THE INVENTION

Problems that the Invention is to Solve

An object of the invention is to provide a polysaccharide derivative that is digestible in vivo, which has high viscoelasticity and is useful as an injectable gel that can be injected into a predetermined location with an injection device such as a syringe. According to previously disclosed techniques, an attempt to increase the proportion of introduced substituents (degree of substitution) in order to obtain a gel having high viscoelasticity causes aggregation or precipitation, and it has been impossible to obtain a highly viscoelastic gel. However, a highly viscoelastic gel, if obtained, can be arbitrarily kept at a specific location in the body for a certain period of time, and thus is useful for protecting wounds or forming physical isolation barriers between organs. Further, by impregnating such a gel with a drug, a local drug delivery system can be achieved. Further, in the case where the gel has such characteristics that it is eventually decomposed or absorbed after injected in vivo, such a gel can be advantageously used as an injectable gel material for use in a surgical operation, a scaffold for regenerative medicine, etc.

Means for Solving the Problems

The inventors conducted extensive research to find an injectable gel that is usable in vivo, is highly safe, and has excellent handleability. As a result, they found that an injectable gel having high viscoelasticity together with excellent handleability can be obtained by chemically modifying carboxyl groups of a carboxy polysaccharide with specific functional groups. They further continued with the research, and accomplished the invention.

That is, the invention is a derivative of a carboxy polysaccharide, some of the carboxyl groups of the carboxy polysaccharide being substituted with —NH—X—CO—Y—Z     (a)

wherein X is a $C_{1-10}$ divalent hydrocarbon group, Y is a divalent group derived from a polyalkylene oxide having oxygen atoms at both ends, and Z is a $C_{1-24}$ hydrocarbon group or —CO—$R^2$, with $R^2$ being a $C_{1-23}$ hydrocarbon group.

Here, "some of the carboxyl groups" refers to some of the plurality of carboxyl groups that a carboxy polysaccharide has, and a carboxyl group being "substituted" means that the carbonyl group in such a carboxyl group is bonded to a substituted amino group represented by the formula (a), forming an amide.

Advantage of the Invention

The injectable gel of the invention is a gel having high viscoelasticity and excellent handleability, and is suitable for use as a medical material such as a sealant for covering wounds and injured regions or an adhesion barrier gel. Further, the injectable gel of the invention can be mixed with cells or proteins, and thus is useful as a scaffold for introducing in vitro cultured cells into the body, a DDS carrier, or the like.

Mode for Carrying Out the Invention

"Carboxy polysaccharide" in the invention refers to a polysaccharide having carboxyl groups in side chains. Specific examples thereof include natural polysaccharides such as hyaluronic acid, alginic acid, pectin, and polygalacturonic acid, carboxyalkyl polysaccharides such as carboxymethyl pullulan, carboxymethyl chitin, carboxymethyl chitosan, carboxymethyl mannan, carboxymethyl starch, and carboxymethyl dextran, and oxidized polysaccharides such as oxidized cellulose and oxidized starch.

As a carboxy polysaccharide, hyaluronic acid is preferable. In such a case, a hyaluronic acid derivative having as a repeating unit a chemical structure represented by the following formula can be mentioned as an example.

In the formula, R is a group represented by the following

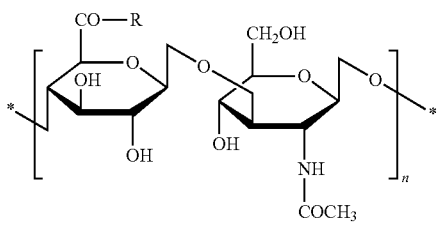

(a) or (b), and at least a part of R's is a group represented by (a).

—NH—X—CO—Y—Z    (a)

—OM    (b)

M is a hydrogen atom, an alkali metal, or an alkaline-earth metal.

Examples of alkali metals include sodium, potassium, and lithium, and examples of alkaline-earth metals include magnesium and calcium. Sodium is preferable.

X in the formula (a) is a $C_{1-10}$ divalent hydrocarbon group. Specific examples thereof include a methylene group, an ethylene group, an n-propylene group, an isopropylene group, an n-butylene group, and an isobutylene group. A methylene group is preferable.

Y is a divalent group derived from a polyalkylene oxide having oxygen atoms at both ends. A polyalkylene oxide specifically refers to a polyalkylene ether, such as polyethylene glycol, polypropylene glycol, or polybutylene glycol. It is preferable that the alkylene moiety of the polyalkylene oxide has a carbon number of 2 to 4. Having oxygen atoms at both ends refers to a structure in which both terminal hydroxyl groups of a polyalkylene oxide with the hydrogen atoms removed are involved in bonding with adjacent groups. Specific examples thereof include groups derived from 1,2-polypropylene glycols represented by —(O—CH$_2$—CH(CH$_3$)—)$_p$—O—, 1,3-polypropylene glycols represented by —(O—CH$_2$—CH$_2$—CH$_2$—)$_p$—O—, polyethylene glycols represented by —(O—CH$_2$—CH$_2$—)$_p$—O—, etc. Further, groups derived from copolymers of a polyethylene glycol and a polypropylene glycol as mentioned above, such as a copolymer represented by PEO-PPO, are also possible. Here, p represents the number of repeating units. The number of repeating units p is preferably 2 to 100, and still more preferably 3 to 70.

Z is a $C_{1-24}$ hydrocarbon group or —CO—$R^2$, and $R^2$ is a $C_{1-23}$ hydrocarbon group.

Specific examples of $C_{1-24}$ hydrocarbon groups for Z include straight alkyl groups such as a methyl group, an ethyl group, a propyl group, a butyl group, a pentyl group, a hexyl group, an octyl group, a nonyl group, a lauryl group, and a stearyl group; alkyl groups having a cyclic structure, such as a cyclohexyl group, a cyclopentyl group, a cyclohexylnonyl group, and a cholesteryl group; unsaturated alkyl groups such as an oleyl group; and aromatic hydrocarbon groups such as a phenyl group, a naphthyl group, and a benzyl group. Among these, a stearyl group, an oleyl group, and the like are preferable.

$R^2$ is a $C_{1-23}$ hydrocarbon group. Specific examples of $R^2$ include straight alkyl groups such as a methyl group, an ethyl group, a propyl group, a butyl group, a pentyl group, a hexyl group, an octyl group, a nonyl group, a heptadecanyl group, a heptadecenyl group, a lauryl group, and a stearyl group; alkyl groups having a cyclic structure, such as a cyclohexyl group, a cyclopentyl group, a cyclohexylnonyl group, and a cholesteryl group; unsaturated alkyl groups such as an oleyl group; and aromatic hydrocarbon groups such as a phenyl group, a naphthyl group, and a benzyl group. Among these, a heptadecanyl group, a heptadecenyl group, and the like are preferable.

In the case where $R^2$ is an aliphatic alkyl group, —CO—$R^2$ for Z is an acyl group derived from a fatty acid. Preferred specific examples of such acyl groups include a lauroyl group, a palmitoyl group, a stearoyl group, and an oleoyl group. Meanwhile, when $R^2$ is an aromatic group, —CO—$R^2$ for Z is an acyl group derived from an aromatic fatty acid. Preferred specific examples thereof include a benzoyl group and a naphthoyl group. Among these, a stearoyl group and an oleoyl group are preferably used.

The degree of substitution in the invention refers to the equivalent weight of the substituent (a), taking the total equivalent weight of the substituent (a) and the substituent (b) as 1. The degree of substitution of the substituent (a) is preferably 0.01 to 0.80, more preferably 0.03 to 0.60, and still more preferably 0.05 to 0.40.

When the degree of substitution of the substituent (a) is controlled within this range, a gel that has excellent viscoelasticity and can be injected using an instrument having a small tube, such as a syringe, can be obtained. The degree of substitution of the substituent (a) can be determined from the ratio between carbon content and nitrogen content by elemental analysis.

Further, the weight-average molecular weight of the polysaccharide derivative is $5 \times 10^3$ to $5 \times 10^6$, preferably $5 \times 10^4$ to $5 \times 10^6$, and more preferably $5 \times 10^4$ to $1 \times 10^6$. With respect to the weight-average molecular weight of the polysaccharide derivative, the introduction of the substituent (a) to be introduced causes a change in molecular weight, and the molecular weight increases from that of a carboxy polysaccharide before the introduction of the substituent (a). By appropriately selecting the molecular weight of the raw material carboxy polysaccharide, a polysaccharide derivative having a desired molecular weight can be obtained.

The raw material polysaccharide may be of animal origin or plant origin, or may also be a polysaccharide produced by a fermentation process. When carboxyl groups are introduced thereinto by chemical modification, the synthesis method is not particularly limited.

The derivative of a carboxy polysaccharide of the invention can be obtained by a condensation reaction between (i) a carboxy polysaccharide or a metal salt thereof and (ii) a component P represented by the following formula (2).

Here, the component P is a compound having an amino group at one end, which is represented by the following formula (2):

$$H_2N—X—CO—Y—Z \quad (2)$$

Here, the definition of X, Y, and Z is the same as in the above formula (a).

The amino group is not particularly limited, and may form a salt with an appropriate acid or may also be a free amino group. Preferably, a compound represented by formula (2) can be produced by the following reactions. A represents a protective group of an amino group.

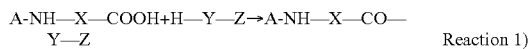
$$A\text{-}NH—X—COOH + H—Y—Z \rightarrow A\text{-}NH—X—CO—Y—Z \quad \text{Reaction 1)}$$

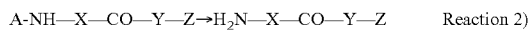
$$A\text{-}NH—X—CO—Y—Z \rightarrow H_2N—X—CO—Y—Z \quad \text{Reaction 2)}$$

The reaction 1) is a coupling reaction between an amino acid derivative having a protected amino group, which is represented by A-NH—X—COO—, and a compound having a hydroxyl group at one end, which has the structure H—Y—Z. In the reaction, it is preferable to use a condensing agent that forms an ester bond. A condensing agent such as a carbodiimide is preferably used. A preferred specific example thereof is dicyclohexylcarbodiimide.

The protective group A of the amino group may be a known protective group, such as a benzyl group or a t-butyloxycarbonyl group (Boc group), specifically. Among these, a Boc group is preferable.

For A-NH—X—CO—Y—Z obtained from the reaction 1), not only the above coupling reaction (reaction 1)) but also any known synthesis methods are usable. For example, it may be synthesized by an ester exchange reaction of an amino acid derivative having a protected amino group and an active-esterified carboxyl group with a compound having a hydroxyl group at one end, which has the structure H—Y—Z.

The reaction 2) is an amino group deprotection reaction, and may be any reaction as long as it is a known reaction employed in ordinary peptide synthesis. In the case where A is a Boc group, a deprotection reaction using an acid is desirable, and an acid such as trifluoroacetic acid is preferably used. The method for purifying the reaction product is not particularly limited either, and separation and purification by chromatography can be performed if desired.

The reactions 1) and 2) may be liquid-phase synthesis or solid-phase synthesis, and the reaction method and the purification method are not particularly limited.

As a result of a coupling reaction between the amino group at one end of $H_2N$—X—CO—Y—Z that is the compound obtained by the above reactions and a carboxyl group of a carboxy polysaccharide, the polysaccharide derivative of the invention is obtained.

$H_2N$—X—CO—Y—Z is introduced into a reaction system such that the amount thereof is 0.01 to 0.8 equivalents based on the molar equivalents of the carboxyl groups of a carboxy polysaccharide, the starting material. At this time, in consideration of reaction efficiency, the amount of $H_2N$—X—CO—Y—Z used may be in excess.

For the characteristics of a carboxy polysaccharide, it is preferable that the coupling reaction is carried out in a solution containing water. In this case, the reaction solvent may be only water or may also be mixed with a water-compatible organic solvent. The reaction may also be carried out in a two-phase system using a water-incompatible organic solvent. Examples of water-compatible organic solvents include alcohols such as methanol and ethanol, cyclic ethers such as tetrahydrofuran and dioxane, ethers such as polyethylene oxide compounds, amides such as dimethylformamide and dimethylacetamide, organic bases such as pyridine and piperidine, dialkyl sulfones such as dimethyl sulfoxide, and ketones such as acetone. Preferably, the reaction between a carboxy polysaccharide and $H_2N$—X—CO—Y—Z is preferably carried out in a uniform reaction system obtained by mixing water with a water-compatible organic solvent, and tetrahydrofuran is preferable as the water-compatible organic solvent.

The catalyst used for coupling may be any of known compounds, and a carboxyl activating agent or a condensing agent is preferably used. Examples of carboxyl activating agents include N-hydroxysuccinimide, p-nitrophenol, N-hydroxybenzotriazole, N-hydroxypiperidine, N-hydroxysuccinamide, 2,4,5-trichlorophenol, and N,N-dimethylaminopyridine. Examples of condensing agents include 1-ethyl-3-(dimethylaminopropyl)-carbodiimide and hydrochlorides thereof, diisopropylcarbodiimide, dicyclohexylcarbodiimide, and N-hydroxy-5-norbornene-2,3-dicarboximide.

Among these, it is preferable to use N-hydroxybenzotriazole as a carboxy activating agent and a hydrochloride of 1-ethyl-3-(dimethylaminopropyl)-carbodiimide as a condensing agent.

The reaction temperature is preferably 0 to 60° C. In order to inhibit by-products, it is more preferable to carry out the reaction at 0 to 10° C. The reaction environment is preferably weakly acidic, and more preferably pH 6 to 7.

The hydrogel of the invention is a hydrogel formed when the carboxy polysaccharide derivative of the invention takes in water. The hydrogel contains, per 100 parts by weight of water, 0.05 to 3.0 parts by weight, preferably 0.1 to 2.0 parts by weight, still more preferably 0.3 to 1.0 parts by weight, of the carboxy polysaccharide derivative.

Of hydrogels of the invention, a preferred hydrogel has viscoelasticity at such a level that it does not flow off when a container of the gel is tilted. Also, a preferred hydrogel easily deforms when touched with a metal spatula, such as a spatula, is in such a state that it can be easily applied to affected areas, and can be injected with an instrument having a small tube, such as a syringe. The viscoelasticity of the hydrogel of the invention can be adjusted by changing the amount of the carboxy polysaccharide derivative of the invention relative to water, and thus can be optimized according to the intended use.

Further, the hydrogel of the invention is transparent and colorless. In industrial production, this is advantageous in that when foreign substances, such as dust, are incorporated in the process of production, such foreign substances can be detected.

Further, when the hydrogel of the invention is diluted with water, the gel absorbs water, and the volume of the gel increases with an increase in the amount of water. The hydrogel of the invention has such a characteristic that as the hydrogel is further diluted with water, it is eventually solubilized in water, loses its gel properties, and becomes an aqueous solution.

Components contained in the hydrogel of the invention other than water include a condensing agent or the like used as a catalyst, by-products such as urea produced by a condensing agent undergoing a predetermined chemical reaction, a carboxyl activating agent, unreacted amines, foreign substances that may be incorporated in each stage of the reaction, ions used for pH adjustment, etc. It is preferable that the levels of these components are kept not higher than the contents so low that their entry into the body is not recognized as a foreign-body reaction.

The hydrogel obtained from the carboxy polysaccharide derivative of the invention preferably has a complex modulus of 50 to 900 N/m$^2$, more preferably 100 to 700 N/m$^2$, as measured using a dynamic viscoelasticity measuring apparatus (rheometer) at an angular velocity of 10 rad/sec under the condition where the polymer concentration in water is 0.5% by weight and the temperature is 37° C. Here, a complex modulus refers to a constant that represents a ratio between the stress and strain of an elastic body.

When chemical species are appropriately selected, the carboxy polysaccharide of the invention shows temperature responsiveness. Temperature responsiveness refers to such a characteristic that when a temperature change is provided to a hydrogel of the carboxy polysaccharide derivative, the viscosity of the gel increases or decreases after the temperature reaches a specific point. In particular, a hydrogel whose viscosity increases after the temperature reaches about 30° C., which is near body temperature, can be advantageously used as an injectable gel for injection into the body. As a preferred example of the polysaccharide derivative having temperature responsiveness of the invention, one in which the polysaccharide is hyaluronic acid, Y in the formula (a) is polyethylene oxide, and the number of repeating units p is 5 to 40 can be mentioned.

The temperature responsiveness of the polysaccharide derivative of the invention is affected by the kind of polysaccharide, the degree of substitution, the kinds and lengths of side chains, and the like. However, a person skilled in the art who has an understanding of factors to be considered for the preparation of a polysaccharide derivative having temperature responsiveness can also readily obtain, through a simple experiment, a carboxyl polysaccharide having temperature responsiveness other than the hyaluronic acid derivative mentioned above.

As applications of the carboxy polysaccharide derivative and hydrogels thereof of the invention, they can be used for medical applications including biomedical materials, commodity applications and cosmetic applications such as hair care products and skin moisturizers, and the like. In particular, because the hydrogel of the invention is injectable through a syringe, it can be used for minimally invasive medicine. Particularly, it can be advantageously used as a carrier of cells for regenerative medicine, a carrier for the retention/sustained-release of humoral factors such as growth factors, a carrier for the retention/sustained-release of low-molecular compounds usable as drugs, or a biomedical material such as an adhesion barrier or a sealant. Further, it is suitable for use as a cell culture carrier, a microbial culture carrier, a dental implant material, and the like. A complex of a shaped product, in which cells have been cultured, with the cells can be advantageously used as a cell chip or the like for sensing, diagnosis, etc.

The carboxy polysaccharide derivative and hydrogels thereof of the invention can be sterilized by any of known sterilization methods. Preferred sterilization methods are gas sterilization by electron beam irradiation or ethylene oxide, autoclave sterilization, and the like.

EXAMPLES

Example 1

Synthesis of $H_2N-CH_2-CO-(O-CH_2CH_2)_7-O-C_{18}H_{35}$

To 1 mmol of oleyl alcohol polyethylene glycol ether (H—(O—CH$_2$CH$_2$)$_7$—O—C$_{18}$H$_{35}$, manufactured by Wako Pure Chemical Industries), a dichloromethane solution prepared by dissolving 1 mmol of N-butyloxycarbonyl glycine (Boc-Gly-OH, manufactured by Wako Pure Chemical Industries) in dichloromethane and containing 1 mmol of dicyclohexylcarbodiimide (manufactured by Wako Pure Chemical Industries) as a condensing agent was added dropwise at room temperature. The reaction mixture was filtered to remove dicyclohexylurea, a by-product, followed by concentration and drying to give an intermediate having a protected amino group (Boc-NH—CH$_2$—CO—(O—CH$_2$CH$_2$)$_7$—O—C$_{18}$H$_{35}$).

To the intermediate was added about 1 to 2 ml of trifluoroacetic acid (manufactured by Wako Pure Chemical Industries), and a de-Boc reaction by acid treatment was carried out at room temperature for 2 hours. The progress of the reaction was checked by TLC. The reaction mixture was concentrated under reduced pressure, and excess trifluoroacetic acid was removed. A trifluoroacetate of an amine compound, the target product, was thus obtained. The product was identified by $^1$H-NMR.

Example 2

Coupling of Hyaluronic Acid (HA-Na) and $H_2N-CH_2-CO-(O-CH_2CH_2)_7-O-C_{18}H_{35}$ 200 mg of HA-Na (FCH120, manufactured by Kibun Food Chemifa) was dissolved in 40 ml of water, and 40 ml of tetrahydrofuran was further added thereto, followed by mixing to give a uniform solution. To the solution was added the trifluoroacetic acid salt of H$_2$N—CH$_2$—CO—(O—CH$_2$CH$_2$)$_7$—O—C$_{18}$H$_{35}$ synthesized in Example 1 in an amount of 0.2 equivalents per equivalent of the carboxyl groups of HA-Na, followed by mixing.

EDC (1-ethyl-3-[3-(dimethylamino)propyl]carbodiimide-HCl, manufactured by WAKO PURE CHEMICAL INDUSTRIES) and HOBt-H$_2$O (1-hydroxybenzotriazole monohydrate, manufactured by WAKO PURE CHEMICAL INDUSTRIES) were dissolved in 10 ml of tetrahydrofuran/water=1/1, each in an amount of 1.1 equivalents based on H$_2$N—CH$_2$—CO—(O—CH$_2$CH$_2$)$_7$—O—C$_{18}$H$_{35}$, and added to the reaction system, followed by stirring overnight. After stirring, the reaction mixture was concentrated on a rotary evaporator to remove tetrahydrofuran, water was evaporated, and, when the total volume was concentrated to about ⅓ the original volume, the reaction solution was added to ethanol to cause precipitation. The precipitate was removed by filtration. The precipitate was suspended in ethanol, and stirred for 24 hours. The precipitate was then collected, and vacuum-dried to give 136 mg of a hyaluronic acid derivative. The obtained hyaluronic acid derivative was subjected to elemental analysis, and the degree of substitution was calculated from the ratio between carbon and nitrogen. As a result, the degree of substitution was 0.09.

Example 3

Preparation of Hydrogel 10 mg of the hyaluronic acid derivative obtained in Example 2 was dissolved in 990 mg of ion-exchange water to prepare a hydrogel with a concentration of 1.0% by weight. The obtained hydrogel was transparent and colorless, did not flow even when the container was tilted, allowed a metal spatula, such as a spatula, to be easily inserted therein, and was easily extruded through a 25 G injection needle.

Further, the complex modulus of the obtained hydrogel was measured. The result was 365 N/m². Using a dynamic viscoelasticity measuring apparatus Rheometer RFIII (TA Instrument), the complex modulus of the hydrogel was measured using a measuring instrument with cone and plate geometry (Φ25 mm) at 37° C. and an angular velocity of 10 rad/sec.

Example 4

Temperature Responsiveness of Hydrogel

The hydrogel obtained in Example 2 was placed in the dynamic viscoelasticity measuring apparatus of Example 3, and the temperature of the sample was increased from 20° C. while measuring dynamic viscoelasticity at an angular velocity of 10 rad/sec. As a result, from 30° C. to 55° C., the complex modulus increased from 281 N/m² to 909 N/m². It was thus confirmed that the gel shows temperature responsiveness, and that the complex modulus increases with an increase in temperature.

Thus, the hydrogel shows temperature responsiveness, and its complex modulus increases at a temperature near body temperature. Therefore, the hydrogel can be advantageously used for retention at a specific location in the body.

INDUSTRIAL APPLICABILITY

The carboxy polysaccharide derivative of the invention forms a hydrogel having high viscoelasticity, and thus can stay at a specific location in the body. Therefore, it is used for protecting wounds or forming physical isolation barriers between organs.

Further, by impregnating the hydrogel of the invention with a drug, a local drug delivery system can be achieved.

Further, the hydrogel of the invention has such characteristics that it is eventually decomposed or absorbed after injected in vivo, and thus can be advantageously used as an injectable gel material for use in a surgical operation, a scaffold for regenerative medicine, etc.

As other applications, uses as commodities and cosmetics, such as hair care products and skin moisturizers, are possible, for example. Further, applications to cell culture carriers, microbial culture carriers, dental implant materials, and the like are also possible. Further, a complex of a shaped product, in which cells have been cultured, with the cells can be used as a cell chip or the like for sensing, diagnosis, etc.

The invention claimed is:

1. A carboxy polysaccharide, some of the carboxyl groups of the carboxy polysaccharide being substituted with —NH—X—CO—Y—Z (a)

wherein X is a $C_{1-4}$ divalent hydrocarbon group, Y is —O—((alkylene group)-O—)$_n$- wherein n is an integer from 2 to 100, and Z is a $C_{12-18}$ hydrocarbon group or —CO—$R^2$, with $R^2$ being a $C_{11-17}$ hydrocarbon group.

2. The polysaccharide according to claim 1, wherein the carboxy polysaccharide is hyaluronic acid.

3. The polysaccharide according to claim 1, wherein the degree of substitution of the substituent (a) is 0.01 to 0.80.

4. A hydrogel comprising the polysaccharide according to claim 1 in an amount of 0.1 to 2.0 parts by weight per 100 parts by weight of water.

5. The hydrogel according to claim 4, characterized by having temperature responsiveness.

6. A medical material comprising the polysaccharide according to claim 1.

7. An adhesion barrier comprising the polysaccharide according to claim 1.

8. The polysaccharide according to claim 2, wherein the degree of substitution of the substituent (a) is 0.01 to 0.80.

9. A hydrogel comprising the polysaccharide according to claim 2 in an amount of 0.1 to 2.0 parts by weight per 100 parts by weight of water.

10. A hydrogel comprising the polysaccharide according to claim 3 in an amount of 0.1 to 2.0 parts by weight per 100 parts by weight of water.

11. A hydrogel comprising the polysaccharide according to claim 8 in an amount of 0.1 to 2.0 parts by weight per 100 parts by weight of water.

* * * * *